United States Patent

Santel et al.

[11] Patent Number: 5,811,373
[45] Date of Patent: Sep. 22, 1998

[54] SELECTIVE HERBICIDES BASED ON CARBAMOYLTRIAZOLINONES AND HETEROARYLOXYACETAMIDES

[75] Inventors: Hans-Joachim Santel, Leverkusen; Heinz Förster, Kadenbach; Klaus-Helmut Müller, Düsseldorf, all of Germany

[73] Assignee: Bayer Aktiengesellschaft, Leverkusen, Germany

[21] Appl. No.: 817,361

[22] PCT Filed: Oct. 4, 1995

[86] PCT No.: PCT/EP95/03906

§ 371 Date: Apr. 10, 1997

§ 102(e) Date: Apr. 10, 1997

[87] PCT Pub. No.: WO96/11575

PCT Pub. Date: Apr. 25, 1996

[30] Foreign Application Priority Data

Oct. 17, 1994 [DE] Germany ............ 44 37 049.0

[51] Int. Cl.⁶ ............ A01N 43/653; A01N 43/824
[52] U.S. Cl. ............ 504/139
[58] Field of Search ............ 504/139

[56] References Cited

U.S. PATENT DOCUMENTS 4,968,342  11/1990  Förster et al. ............ 71/90
5,593,942  1/1997   Santel et al. ............ 504/134

FOREIGN PATENT DOCUMENTS 0 294 666    12/1988  European Pat. Off. ....... A01N 47/38
0 348 737 A1  1/1990  European Pat. Off. ....... A01N 43/76
0 445 420 A2  9/1991  European Pat. Off. ....... A01N 47/38
WO 94/02014   2/1994  WIPO .

OTHER PUBLICATIONS

CA 116:36252m (1992) Lindig et al., "Selective synergistic herbicides containing . . . derivative,".

*Primary Examiner*—S. Mark Clardy
*Attorney, Agent, or Firm*—Sprung Kramer Schaefer & Briscoe

[57] ABSTRACT

The new herbicidal active compound combinations composed of (1) a carbamoyltriazolinone of the formula (I) and (2) a heteroaryloxyacetamide of the formula (II)

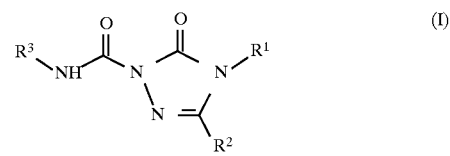

and

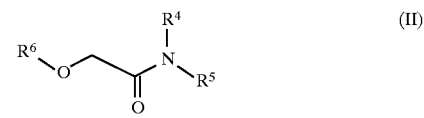

in which $R^6$ represents optionally substituted heteroaryl and $R^1$–$R^5$ have the meanings given in the description show, when used in certain ratios by weight, synergistic effects and can be employed as selective herbicides in a variety of crops of useful plants (for example maize and soya), good control also being effected on plants which are otherwise problem weeds, such as Portulaca and Xanthium species.

5 Claims, No Drawings

SELECTIVE HERBICIDES BASED ON CARBAMOYLTRIAZOLINONES AND HETEROARYLOXYACETAMIDES

This application has been filed under 35USC371 as the national stage of international application PCT/EP95/03906, filed Oct. 4, 1995.

The invention relates to new herbicidal synergistic active compound combinations composed, on the one hand, of known carbamoyltriazolinones and, on the other hand, known heteroaryloxyacetamides, which can be used particularly successfully for selectively combating weeds in a variety of crops of useful plants.

Carbamoyltriazolinones, which are herbicides with a broad spectrum of action, are the subject of a series of patent applications (cf EP-A 294666, EP-A 370293, EP-A 391187, EP-A 398096, EP-A 399294, EP-A 415196, EP-A 477646). However, the known carbamoyltriazolinones are incomplete with regard to their action in many ways, in particular regarding monocotyledon weeds.

Heteroaryloxyacetamides, being powerful herbicides which are particularly effective against monocotyledon weeds, are also the subject of a series of patent applications (cf. EP-A 5501, EP-A 18497, EP-A 29171, EP-A 94514, EP-A 100044, EP-A 100045, EP-A 161602, EP-A 195237, EP-A 348734, EP-A 348737). However, the known heteroaryloxyacetamides are not equally effective against all monocotyledon weeds.

Surprisingly, it has now been found that a series of known herbicidal active compounds from the group of the carbamoyltriazolinones when used together with known herbicidal active compounds from the group of the heteroaryloxyacetamides have pronounced synergistic effects regarding the activity against weeds and can be used particularly advantageously as broad-spectrum combination preparations for selectively combating both monocotyledon and dicotyledon weeds pre-and post-emergence in crops of monocotyledon and dicotyledon useful plants, such as, for example, maize and soya.

The invention relates to synergistic herbicidal compositions, characterized by an effective content of a combination of active compounds composed of
(1) a carbamoyltriazolinone of the general formula (I)

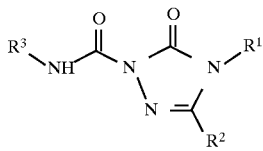

in which
$R^1$ represents hydrogen, hydroxyl, amino, or in each case optionally substituted alkyl, alkenyl, alkinyl, alkoxy, alkenyloxy, alkinyloxy, alkylamino, alkenylamino, alkinylamino, alkylideneamino, dialkylamino, cycloalkyl, cycloalkylalkyl, aryl or arylalkyl,
$R^2$ represents in each case optionally substituted alkyl, alkenyl, alkinyl, alkoxy, alkenyloxy, alkinyloxy, alkylthio, alkenylthio, alkinylthio, alkylamino, alkenylamino, alkinylamino, dialkylamino, cycloalkyl, cycloalkyloxy, cycloalkylalkyl, aryl, aryloxy, arylthio, arylamino or arylalkyl, and
$R^3$ represents in each case optionally substituted alkyl, alkenyl, alkinyl, cycloalkyl, cycloalkylalkyl, arylalkyl, arylalkenyl or arylalkinyl,
and (2) a heteroaryloxyacetamide of the general formula (II)

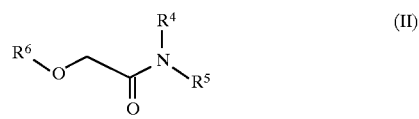

in which
$R^4$ represents in each case optionally substituted alkyl, alkenyl, alkinyl or alkoxy,
$R^5$ represents in each case optionally substituted alkyl, alkenyl, alkinyl or phenyl, and
$R^6$ represents optionally substituted heteroaryl,
0.001 to 1000 parts by weight of active compound of the general formula (II) generally being used relative to 1 part by weight of active compound of the general formula (I).

Herbicidal compositions according to the invention which are of particular interest are those which are characterized by a content of a combination of active compounds composed of (1) a carbamoyltriazolinone of the formula (I) in which
$R^1$ represents hydrogen, hydroxyl, amino, or represents alkyl, alkenyl, alkinyl, alkoxy, alkenyloxy, alkinyloxy, alkylamino, alkenylamino, alkinylamino, alkylideneamino or dialkylamino, each of which has up to 6 carbon atoms and each of which is optionally substituted by halogen or cyano, or represents cycloalkyl or cycloalkylalkyl, each of which has 3 to 6 carbon atoms in the cycloalkyl groups and, if appropriate, I to 4 carbon atoms in the alkyl group and each of which is optionally substituted by halogen, cyano or $C_1$—$C_4$-alkyl, or represents phenyl or phenyl-$C_1$—$C_4$-alkyl, each of which is optionally substituted by halogen, cyano, $C_1$—$C_4$-alkyl or $C_1$—$C_4$-alkoxy.
$R^2$ represents alkyl, alkenyl, alkinyl, alkoxy, alkenyloxy, alkinyloxy, alkylthio, alkenylthio, alkinylthio, alkylamino, alkenylamino, alkinylamino or dialkylamino, each of which has up to 6 carbon atoms and each of which is optionally substituted by halogen, cyano, $C_1$—$C_4$-alkoxy or $C_1$—$C_4$-alkylthio, or represents cycloalkyl, cycloalkyloxy or cycloalkylalkyl, each of which has 3 to 6 carbon atoms in the cycloalkyl groups and, if appropriate, 1 to 4 carbon atoms in the alkyl group and each of which is optionally substituted by halogen, cyano or $C_1$—$C_4$-alkyl, or represents phenyl, phenoxy, phenylthio, phenylamino or phenyl-$C_1$—$C_4$-alkyl, each of which is optionally substituted by halogen, cyano, $C_1$—$C_4$-alkyl or $C_1$—$C_4$-alkoxy and
$R^3$ represents alkyl, alkenyl or alkinyl, each of which has up to 10 carbon atoms and each of which is optionally substituted by halogen, cyano, $C_1$—$C_4$-alkoxy, $C_1$—$C_4$-alkylthio, $C_1$—$C_4$-alkylsulphinyl, $C_1$—$C_4$-alkylsulphonyl, $C_1$—$C_4$-alkylamino or di-($C_1$—$C_4$-alkyl)-amino, or represents cycloalkyl or cycloalkylalkyl, each of which has 3 to 6 carbon atoms in the cycloalkyl moiety and, if appropriate, 1 to 4 carbon atoms in the alkyl moiety and each of which is optionally substituted by halogen, cyano or $C_1$—$C_4$-alkyl, or represents phenyl-$C_1$—$C_6$-alkyl, phenyl-$C_2$—$C_6$-alkenyl or phenyl-$C_2$—$C_6$-alkinyl, each of which is optionally substituted by halogen, cyano, $C_1$—$C_4$-alkyl or $C_1$—$C_4$-alkoxy,
and (2) a heteroaryloxyacetamide of the formula (II) in which
$R^4$ represents alkyl, alkenyl, alkinyl or alkoxy, each of which has up to 6 carbon atoms and each of which is optionally substituted by halogen, cyano or $C_1$—$C_4$-alkoxy,
$R_5$ represents alkyl, alkenyl or alkinyl, each of which has up to 6 carbon atoms and each of which is optionally substituted by halogen, cyano or $C_1$—$C_4$-alkoxy, or represents phenyl which is optionally substituted by halogen, cyano, $C_1$—$C_4$-alkyl, $C_1$—$C_4$-halogenoalkyl, $C_1$—$C_4$-alkoxy or $C_1$—$C_4$-halogenoalkoxy, and $R^6$ represents heteroaryl from the series consisting of 1,3-thiazol-2-yl, 1,2,4-thiadiazol-5-yl, 1,3,4-thiadiazol-2-yl, benzoxazol-2-yl and benzothiazol-2-yl, each of which is optionally substituted by halogen, cyano, $C_1$—$C_4$-alkyl, $C_1$—$C_4$-halogenoalkyl, $C_1$—$C_4$-alkoxy or $C_1$—$C_4$-halogenoalkoxy.

Herbicidal compositions according to the invention which are of very particular interest are those which are characterized by a content of a combination of active compounds composed of(1) a carbamoyltriazolinone of the formula (I) in which $R_1$ represents hydrogen, hydroxyl, amino, or represents methyl, ethyl, n-or i-propyl, n-, i-, s-or t-butyl, propenyl, butenyl, propinyl or butinyl, methoxy, ethoxy, n-or i-propoxy, n-, i-, s-or t-butoxy, propenyloxy, butenyloxy, propinyloxy or butinyloxy, methylamino, ethylamino, n-or i-propylamino, n-, i-, s-or t-butylamino, propenylamino, butenylamino, propinylamino or butinylamino, ethylideneamino, propylideneamino, butylideneamino, dimethylamino or diethylamino, each of which is optionally substituted by fluorine, chlorine or cyano, or represents cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, cyano, methyl, ethyl, n-or i-propyl, or represents phenyl or benzyl, each of which is optionally substituted by fluorine, chlorine, bromine, cyano, methyl, ethyl, n-or i-propyl, n-, i-, s-or t-butyl, methoxy or ethoxy, $R^2$ represents methyl, ethyl, n-or i-propyl, n-, i-, s-or t-butyl, propenyl, butenyl, propinyl, butinyl, methoxy, ethoxy, n-or i-propoxy, n-, i-, s-or t-butoxy, propenyloxy, butenyloxy, propinyloxy, butinyloxy, methylthio, ethylthio, n-or i-propylthio, n-, i-, s-or t-butylthio, propenylthio, butenylthio, propinylthio, butinylthio, methylamino, ethylamino, n-or i-propylamino, n-, i-, s-or t-butylamino, propenylamino, butenylamino, propinylamino, butinylamino, dimethylamino or diethylamino, each of which is optionally substituted by fluorine, chlorine, cyano, methoxy, etlioxy, n-or i-propoxy, methylthio, ethylthio, n-or i-propylthio, or represents cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl or cyclohexylmethyl, each of which is optionally substituted by fluorine, chlorine, bromine, cyano, methyl, ethyl, n-or i-propyl, or represents phenyl, phenoxy, phenylthio, phenylamino or benzyl, each of which is optionally substituted by fluorine, chlorine, bromine, cyano, methyl, ethyl, n-or i-propyl, n-, i-, s-or t-butyl, methoxy or ethoxy, and $R^3$ represents methyl, ethyl, n-or i-propyl, n-, i-, s-or t-butyl, propenyl, butenyl, pentenyl, hexenyl, propinyl, butinyl, pentinyl or hexinyl, each of which is optionally substituted by fluorine, chlorine, cyano, methoxy, ethoxy, n-or i-propoxy, n-, i-, s-or t-butoxy, methylthio, ethylthio, n-or i-propylthio, n-, i-, s-or t-butylthio, methylsulphinyl, ethylsulphinyl, methylsulphonyl, ethylsulphonyl, methylamino, ethylamino, n-or i-propylamino, n-, i-, s-or t-butylamino, dimethylamino, diethylamino, dipropylamino or dibutylamino, or represents cyclopropyl, cyclobutyl, cyclopentyl, cyclohexyl, cyclopropylmethyl, cyclobutylmethyl, cyclopentylmethyl, cyclohexylmethyl, cyclohexylethyl or cyclohexylpropyl, each of which is optionally substituted by fluorine, chlorine, bromine, cyano, methyl, ethyl or n-or i-propyl, or represents benzyl, phenylethyl, phenylpropyl, phenylbutyl, phenylethenyl, phenylpropenyl, phenylbutenyl, phenylethinyl, phenylpropinyl or phenyl-butinyl, each of which is optionally substituted by fluorine, chlorine, bromine, cyano, methyl, ethyl, n-or i-propyl, n-, i-, s-or t-butyl, methoxy or ethoxy, and (2) a heteroaryloxyacetamide of the formula (II) in which $R^4$ represents methyl, ethyl, n-or i-propyl, n-, i-or s-butyl, propenyl, butenyl, propinyl, butinyl, methoxy, ethoxy, n-or i-propoxy, n-, i-, s-or t-butoxy, each of which is optionally substituted by fluorine, chlorine, cyano, methoxy or ethoxy, $R_5$ represents methyl, ethyl, n-or i-propyl, n-, i-, s-or t-butyl, n-, i-, s-or t-pentyl, propenyl, butenyl, propinyl or butinyl, each of which is optionally substituted by fluorine, chlorine, cyano, methoxy or ethoxy, or represents phenyl which is optionally substituted by fluorine, chlorine, bromine, cyano, methyl, ethyl, trifluoromethyl, methoxy, ethoxy, difluoromethoxy or trifluoromethoxy, and $R^6$ represents heteroaryl from the series consisting of 1,3-thiazol-2-yl, 1,2,4-thiadiazol-5-yl, 1,3,4-thiadiazol-2-yl, benzoxazol-2-yl and benzothiazol-2-yl, each of which is optionally substituted by fluorine, chlorine, bromine, cyano, methyl, ethyl, n-or i-propyl, n-, i-, s-or t-butyl, difluoromethyl, trifluoromethyl, dichloromethyl, trichloromethyl, methoxy, ethoxy, n-or i-propoxy, n-, i-, s-or t-butoxy, difluoromethoxy or trifluoromethoxy.

Individual examples which may be mentioned of compounds of the formula (I) to be used as components according to the invention for the mixture are:

4-amino-5-methyl-2-(1,1-dimethyl-ethyl-aminocarbonyl)-2,4-dihydro-3H-1,2,4-triazol-3-one, 4-amino-5-ethyl-2-( 1,1-dimethyl-ethyl-amino-carbonyl)-2,4-dihydro-3H-1,2,4-triazol-3-one, 4-amino-5-propyl-2-( 1,1-dimethyl-ethyl-aminocarbonyl)-2,4-dihydro-3H-1,2,4-triazol-3-one, 4-amino-S-i-propyl-2-(1,-dimethyl-ethyl-aminocarbonyl)-2,4-dihydro-3H-1,2,4-triazol-3-one, 4-amino-5-methoxy-2-(1,1-dimethyl-ethyl-aminocarbonyl)-2,4-dihydro-3H-1 ,2,4-triazol-one, 4-amino-5-ethoxy-2-(1,1-dimethyl-ethyl-aminocarbonyl)-2,4-dihydro-3H-1,2,4-triazol-3-one, 4-amino-5-methyl-2-(2-fluoro-1, 1-dimethyl-ethyl-aminocarbonyl)-2,4-dihydro-3H-1,2,4-triazol-3-one, 4-amino-5-ethyl-2-(2-fluoro- 1,1-dimethyl-ethyl-aminocarbonyl)-2,4-dihydro-3H-1,2,4-triazol-3-one, 4-amino-5-n-propyl-2-(2-fluoro-1,1-dimethyl-ethyl-aminocarbonyl)-2,4-dihydro-3H-1 ,2,4-triazol-3-one, 4-amino-5-i-propyl-2-(2-fluoro-1,1-dimethyl-ethyl-aminocarbonyl)-2,4-dihydro-3H-1,2,4-triazol-3-one, 4-amino-5-methoxy-2-(2-fluoro-1,1-dimethyl-ethyl-aminocarbonyl)-2,4-dihydro-3H-1,2,4-triazol-3-one, 4-amino-5-ethoxy-2-(2-fluoro-1,1-dimethyl-ethyl-aminocarbonyl)-2,4-dihydro-3H-1,2,4-triazol-3-one, 4-amino-5-methyl-2-(2-chloro-1, 1-dimethyl-ethyl-aminocarbonyl)-2,4-dihydro-3H-1,2,4-triazol-3-one, 4-amino-5-ethyl-2-(2-chloro-1,1-dimethyl-ethyl-aminocarbonyl)-2,4-dihydro-3H-1,2,4-triazol-3-one, 4-amino-5-n-propyl-2-(2-chloro-1,1-dimethyl-ethyl-aminocarbonyl)-2,4-dihydro-3H-1,2,4-triazol-3-one, 4-amino-5-i-propyl-2-(2-chloro-1,1-dimethyl-ethyl-aminocarbonyl)-2,4-dihydro-3H-1,2,4-triazol-3-one, 4-amino-5-methoxy-2-(2-chloro-1, 1-dimethyl-ethyl-aminocarbonyl)-2,4-dihydro-3H-1,2,4-triazol-3-one, 4-amino-5-ethoxy-2-(2-chloro-1,1-dimethyl-ethyl-aminocarbonyl)-2,4-dihydro-3H-1,2,4-triazol-3-one, 4-amino-5-i-propyl-2-i-propyl-aminocarbonyl-2,4-dihydro-3H-1,2,4-triazol-3-one, 4-amino-5-dimethylamino-2-(1,1-dimethyl-ethyl-amino-carbonyl)-2,4-dihydro-3H-1,2,4-triazol-3-one, 4-amino-5-dimethylamino-2-(2-fluoro-1,1-dimethyl-ethyl-aminocarbonyl)-2,4-dihydro-3H -1,2,4-triazol-3-one, 4-amino-5-dimethylamino-2-(2-chloro-1,1-dimethyl-ethyl-aminocarbonyl)-2,4-dihydro-3H-1,2,4-triazol-3-one and 4-methyl-5-methoxy-2-(1,1-dimethyl-ethyl-aminocarbonyl)-2,4-dihydro-3H -1,2,4-triazol-3-one.

Particular mention as component of the formula (I) in the mixture may be made of the compound 4-amino-5-(1-methyl-ethyl)-2-(1,1-dimethyl-ethyl-aminocarbonyl)-2,4-dihydro-3H-1,2,4-triazol-3-one, termed compound (I-1) in the use examples.

Individual examples which may be mentioned of the compounds of the formula (II) to be used as components according to the invention for the mixture are:
N-methyl-N-phenyl-α-(5-trifluoromethyl-1,3,4-thiadiazol-2-yl-oxy)-acetamide, N-ethyl-N-phenyl-α-(5-trifluoromethyl-1,3,4-thiadiazol-2-yl-oxy)-acetamide, N-n-propyl-N-phenyl-α-(5-trifluoromethyl-1,3,4-thiadiazol-2-yl-oxy)-acetamide, N-i-propyl-N-phenyl-α-(5-trifluoromethyl-1,3,4-thiadiazol-2-yl-oxy)-acetamide, N-methyl-N-(4-fluorophenyl)-α-(5-trifluoromethyl-1,3,4-thiadiazol-2-yl-oxy)-acetamide, N-ethyl-N-(4-fluoro-phenyl)-α-(5-trifluoromethyl-1,3,4-thiadiazol-2-yl-oxy)-acetamide, N-n-propyl-N-(4-fluoro-phenyl)-α-(5-trifluoromethyl-1,3,4-thiadiazol-2-yl-oxy)-acetamide, N-i-propyl-N-(4-fluoro-phenyl)-α-(5-trifluoromethyl-1,3,4-thiadiazol-2-yl-oxy)-acetamide, N-methyl-N-(4-chloro-phenyl)-α-(5-trifluoromethyl-1,3,4-thiadiazol-2-yl-oxy)-acetamide, N-ethyl-N-(4-chloro-phenyl)-α-(5-trifluoromethyl-1,3,4-thiadiazol-2-yl-oxy)-acetamide, N-n-propyl-N-(4-chloro-phenyl)-α-(5-trifluoromethyl-1,3,4-thiadiazol-2-yl-oxy)-acetamide and N-i-propyl-N-(4-chloro-phenyl)-α-(5-trifluoromethyl-1,3,4-thiadiazol-2-yl-oxy)-acetamide.

Particular mention as component of the formula (II) for the mixture may be made of the compound N-i-propyl-N-(4-fluoro-phenyl)-α-(5-trifluoromethyl-1,3,4-thiadiazol-2-yl-oxy)-acetamide, termed compound (II-1) in the use examples.

The compounds of the formula (I) and (II) are described in the abovementioned patent applications or patent specifications.

Surprisingly, it has now been found that the above-defined combinations of active compounds, composed of the carbamoyltriazolinones of the formula (I) and the heteroaryloxyacetamides of the formula (II), have a particularly powerful activity and can be used in a variety of crops for selectively combating weeds.

Surprisingly, the herbicidal activity of the combinations of active compounds according to the invention considerably exceeds the total of the activities of the individual active compounds.

This means that there exists not only a complementary action but a true synergistic effect, which could not have been anticipated. The new combinations of active compounds are tolerated well by a large number of crops, and the action of the new combinations of active compounds also extend effectively to plants which are usually considered as problem weeds, such as Portulaca and Xanthium species. The new combinations of active compounds are therefore a valuable enrichment of the selective herbicides.

The combinations of active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, lpomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the combinations of active compounds according to the invention is in no way restricted to these genera, but also extends in the same manner to other plants.

When the concentrations are in specific ratios, the synergistic effect of the combination of active compounds according to the invention is particularly pronounced. However, the ratios by weight of the active compounds in the combinations of active compounds can be varied within relatively wide ranges. In general, 0.001 to 1000 parts by weight, preferably 0.01 to 100 parts by weight and particularly preferably 0.1 to 10 parts by weight of active compound of the formula (II) are used relative to 1 part by weight of active compound of the formula (I).

The active compounds, or combinations of active compounds, can be converted into the customary formulations, such as solutions, emulsions, wettable powders, suspensions, powders, dusts, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers,. such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs. and trace nutrients such as salts of iron, manganese, boron, copper, cobalt, molybdenum and zinc.

The formulations in general comprise between 0.1 and 95 percent by weight of active compound, preferably between 0.5 and 90%.

In general, the combinations of active compounds according to the invention are applied in the form of ready mixes. However, the active compounds which the active compound combinations comprise can also be formulated individually and mixed upon use, i.e. applied in the form of tank mixes.

The new active compound combinations can be used as such or in the form of their formulations, and furthermore also as mixtures with other known herbicides, ready mixes or tank mixes again being possible. They ma) also be mixed with other known active compounds, such as fungicides, insecticides, acaricides, nematicides, bird repellents, growth substances, plant nutrients and agents which improve soil structure. For particular application purposes, in particular when applied post-emergence, it may furthermore be advantageous to incorporate, in the formulations, mineral or vegetable oils which are tolerated by plants (for example the commercial product "Oleo DuPont 11E") or ammonium salts such as, for example, ammonium sulphate or ammonium rhodanide, as further additives.

The new active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The application rates of the active compound combinations according to the invention can vary within a substantial range; they depend, inter alia, on the weather and on the soil parameters. In general, the application rates are between 5 g and 5 kg per ha, preferably between 20 g and 2 kg per ha, particularly preferably between 50 g and 1.0 kg per ha.

The active compound combinations according to the invention can be applied before and after the plants have emerged, that is to say pre-emergence and post-emergence.

The good herbicidal activity of the new active compound combinations can be seen from the examples which follow. While the individual active compounds show weak points regarding the herbicidal activity, the combinations, without exception, display a very good activity against weeds, which exceeds a simple additive effect.

A synergistic effect in herbicides is always present when the herbicidal activity of the active compound combination exceeds the activity of the active compounds when applied individually.

The expected activity for a given combination of two herbicides can be calculated as follows (cf. COLBY, S. R.: "Calculating synergistic and antagonistic responses of herbicide combinations", Weeds 15, pages 20–22, 1967):
If X=% damage caused by herbicide A (active compound of the formula I) at application rate of p kg/ha
and Y=% damage caused by herbicide B (active compound of the formula II) at application rate of q kg/ha
and E=the expected damage of herbicides A and B at application rates of p and q kg/ha,
then $E = X \pm Y \mp (X*Y/100)$.

If the actually observed damage exceeds the calculated figure, the activity of the combination is superadditive, i.e. it shows a synergistic effect.

It can be seen from the examples which follow that the found herbicidal activity of the active compound combinations according to the invention in the weeds exceeds the calculated activity, i.e. that the new active compound combinations act synergistically.

Use examples:

To prepare the active compound preparations required for the tests, suitable amounts of a water-dispersible powder formulation (WP) of a carbamoyltriazolinone of the formula (I) and of a water-dispersible powder formulation (WP) of a heteroaryloxyacetamide of the formula (II) are weighed and diluted with water to the desired concentration.

In the tests of Tables 1 and 2, 70WP formulations (70% of active compound) of the active compounds in question were in each case employed.

The tests were carried out as follows:
Pre-emergence test/greenhouse

Seeds of the test plant are sown in normal soil and, after 24 hours, watered with the active compound preparation. It is expedient to keep constant the amount of water per unit area. The active concentration in the preparation is of no importance; only the application rate of active compound per unit area being decisive. After the treatment, the test plants are kept in the greenhouse under controlled conditions (temperature, atmospheric humidity, light) until they are evaluated. After three weeks, the degree of damage to the plants is scored in % damage in comparison with the development of untreated control plants.

The figures denote:
0=no action/no damage (like untreated control)
100=total destruction.

Active compounds, application rates and results can be seen in each case from the tables which follow, the abbreviations used in the tables having the following meanings:
fnd.=damage or activity found (in %)
calc.=damage or activity calculated using Colby's formula (in %)
a.i.=active ingredient

TABLE 1

Pre-emergence test/greenhouse

| Active compound or combination | Application rate (in g of a.i./ha) | Soya | | Maize | | Portulaca | | Solanum | | Xanthium | |
|---|---|---|---|---|---|---|---|---|---|---|---|
| | | fnd. | calc. | fnd. | calc. | fnd. | calc. | fnd. | calc. | fnd. | calc. |
| I-1 | 125 | 0 | | 0 | | 80 | | 80 | | 70 | |
| II-1 | 30 | 0 | | 0 | | 0 | | 0 | | 0 | |
| I-1 + II-1 | 125 + 30 | 10 | 0 | 0 | 0 | 100 | 80 | 90 | 80 | 95 | 70 |

TABLE 2

Pre-emergence test/greenhouse

| Active compound or combination | Application rate (in g of a.i./ha) | Soya | | Maize | | Chenopodium | | Portulaca | | Xanthium | |
|---|---|---|---|---|---|---|---|---|---|---|---|
| | | fnd. | calc. | fnd. | calc. | fnd. | calc. | fnd. | calc. | fnd. | calc. |
| I-1 | 60 | 0 | | 0 | | 30 | | 30 | | 0 | |
| II-1 | 30 | 0 | | 0 | | 0 | | 0 | | 0 | |
| I-1 + II-1 | 60 + 30 | 0 | 0 | 0 | 0 | 80 | 30 | 80 | 30 | 80 | 0 |

We claim:

1. A herbicidal composition comprising a combination of compounds containing
    (1) 4-amino-5-(1-methyl-ethyl)-2-(1,1-dimethyl-ethyl-aminocarbonyl)-2,4-dihydro-3H-1,2,4-triazol-3-one as compound I-1 and
    N-i-propyl-N-(4-fluoro-phenyl)-α-(5-trifluoromethyl-1,,3,4-thiadiazol-2-yl-oxy) acetamide as compound II-1, wherein 0.001 to 1000 parts per weight of the compound II-1 is being used relative to 1 part by weight of the compound I-1.

2. The herbicidal composition according to claim 1, wherein in the compound combination, the ratio by weight of the compound I-1 to the compound II-1 is about 1:0.01 to 1:100.

3. The herbicidal composition according to claim 2, wherein the ratio by weight of the compound I-1 to the compound II-1 is about 1:0.1 to 1:10.

4. A method of combating unwanted vegetation which comprises administering to such vegetation or to a locus from which it is desired to exclude such vegetation a herbicidally effective amount of a compound combination according to claim 1.

5. A herbicidal composition comprising a herbicidally effective amount of a compound combination according to claim 1 and an extender.

* * * * *